(12) United States Patent
Schultz et al.

(10) Patent No.: US 7,198,644 B2
(45) Date of Patent: Apr. 3, 2007

(54) INTERVERTEBRAL IMPLANT

(75) Inventors: Robert Schultz, Tuttlingen (DE); Wilhelm Bloemer, Unteruhldingen-Mehlhofen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 294 days.

(21) Appl. No.: 10/880,273

(22) Filed: Jun. 29, 2004

(65) Prior Publication Data
US 2005/0033438 A1 Feb. 10, 2005

(30) Foreign Application Priority Data
Jul. 8, 2003 (DE) ................. 103 30 698

(51) Int. Cl.
*A61F 2/44* (2006.01)
(52) U.S. Cl. ................ 623/17.15; 623/17.16
(58) Field of Classification Search ......... 623/17.11, 623/17.14, 17.15, 23.4
See application file for complete search history.

(56) References Cited

U.S. PATENT DOCUMENTS

| | | |
|---|---|---|
| 3,426,364 A | 2/1969 | Lumb |
| 3,867,728 A | 2/1975 | Stubstad et al. |
| 3,875,595 A | 4/1975 | Froning |
| 4,309,777 A | 1/1982 | Patil |
| 4,759,766 A | 7/1988 | Buettner-Janz et al. |
| 4,759,769 A | 7/1988 | Hedman et al. |
| 4,863,476 A | 9/1989 | Shepperd |
| 4,863,477 A | 9/1989 | Monson |
| 4,911,718 A | 3/1990 | Lee et al. |
| 5,002,576 A | 3/1991 | Fuhrmann et al. |
| 5,122,130 A | 6/1992 | Keller |
| 5,123,926 A | 6/1992 | Pisharodi |

(Continued)

FOREIGN PATENT DOCUMENTS

DE 30 23 353 A1 4/1981

(Continued)

OTHER PUBLICATIONS

Szpalski, Marek, Gunzburg, Robert, and Mayer, Michael, "Spine Arthroplasty: A Historical Review", Eur Spine J (2002), 11 (Suppl. 2), pp. S65-S84.

(Continued)

*Primary Examiner*—Tom Barrett
*Assistant Examiner*—David A. Izquierdo
(74) *Attorney, Agent, or Firm*—RatnerPrestia

(57) ABSTRACT

An intervertebral implant for contact with adjacent vertebral bodies is provided. The implant includes a first carrier plate including a front edge, a middle, a rear edge, and a concave, crowned joint surface comprising a lowest point. The implant further includes a second carrier plate including a front edge, a middle, a rear edge, a center line extending between said front edge and said rear edge, and a convex, crowned joint surface comprising a highest point. The joint surfaces are positioned flatly in contact with one another and are configured to support the carrier plates pivotably with respect to one another. The highest and lowest points of the joint surfaces are positioned between the rear edges and the middles of the carrier plates. The convex joint surface projects farther away from the second carrier plate at its end facing the rear edge than at its end facing the front edge.

9 Claims, 3 Drawing Sheets

U.S. PATENT DOCUMENTS

| | | |
|---|---|---|
| 5,236,460 A | 8/1993 | Barber |
| 5,258,031 A | 11/1993 | Salib et al. |
| 5,306,308 A | 4/1994 | Gross et al. |
| 5,314,477 A | 5/1994 | Marnay |
| 5,370,697 A | 12/1994 | Baumgartner |
| 5,401,269 A | 3/1995 | Büttner-Janz et al. |
| 5,425,773 A * | 6/1995 | Boyd et al. ............... 623/17.15 |
| 5,507,816 A | 4/1996 | Bullivant |
| 5,534,030 A | 7/1996 | Navarro et al. |
| 5,556,431 A | 9/1996 | Büttner-Janz |
| 5,562,738 A | 10/1996 | Boyd et al. |
| 5,674,294 A | 10/1997 | Bainville et al. |
| 5,674,296 A | 10/1997 | Bryan et al. |
| 5,676,635 A | 10/1997 | Levin |
| 5,676,701 A | 10/1997 | Yuan et al. |
| 5,683,465 A | 11/1997 | Shinn et al. |
| 5,702,449 A | 12/1997 | McKay |
| 5,782,830 A | 7/1998 | Farris |
| 5,782,832 A | 7/1998 | Larsen et al. |
| 5,824,094 A | 10/1998 | Serhan et al. |
| 5,827,328 A | 10/1998 | Buttermann |
| 5,865,846 A | 2/1999 | Bryan et al. |
| 5,888,226 A | 3/1999 | Rogozinski |
| 5,888,227 A | 3/1999 | Cottle |
| 5,893,889 A | 4/1999 | Harrington |
| 5,989,291 A | 11/1999 | Ralph et al. |
| 6,001,130 A | 12/1999 | Bryan et al. |
| 6,019,793 A | 2/2000 | Perren et al. |
| 6,039,763 A | 3/2000 | Shelokov |
| 6,063,121 A | 5/2000 | Xavier et al. |
| 6,083,225 A | 7/2000 | Winslow et al. |
| 6,113,637 A | 9/2000 | Gill et al. |
| 6,113,639 A | 9/2000 | Ray et al. |
| 6,127,597 A | 10/2000 | Beyar et al. |
| 6,139,579 A | 10/2000 | Steffee et al. |
| 6,156,067 A | 12/2000 | Bryan et al. |
| 6,162,252 A | 12/2000 | Kuras et al. |
| 6,176,881 B1 | 1/2001 | Schär et al. |
| 6,200,322 B1 | 3/2001 | Branch et al. |
| 6,210,442 B1 | 4/2001 | Wing et al. |
| 6,231,609 B1 | 5/2001 | Mehdizadeh |
| 6,296,664 B1 | 10/2001 | Middleton |
| 6,348,071 B1 | 2/2002 | Steffee et al. |
| 6,368,350 B1 | 4/2002 | Erickson et al. |
| 6,395,032 B1 | 5/2002 | Gauchet |
| 6,419,706 B1 | 7/2002 | Graf |
| 6,443,987 B1 | 9/2002 | Bryan |
| 6,443,990 B1 | 9/2002 | Aebi et al. |
| 6,468,310 B1 | 10/2002 | Ralph et al. |
| 6,517,580 B1 | 2/2003 | Ramadan et al. |
| 6,524,341 B2 | 2/2003 | Läng et al. |
| 6,527,804 B1 | 3/2003 | Gauchet et al. |
| 6,527,806 B2 | 3/2003 | Ralph et al. |
| 6,533,818 B1 | 3/2003 | Weber et al. |
| 6,540,785 B1 | 4/2003 | Gill et al. |
| 6,558,424 B2 | 5/2003 | Thalgott |
| 6,562,072 B1 | 5/2003 | Fuss et al. |
| 6,572,653 B1 | 6/2003 | Simonson |
| 6,575,899 B1 | 6/2003 | Foley et al. |
| 6,579,320 B1 | 6/2003 | Gauchet et al. |
| 6,579,321 B1 | 6/2003 | Gordon et al. |
| 6,582,466 B1 | 6/2003 | Gauchet |
| 6,582,468 B1 | 6/2003 | Gauchet |
| 6,607,558 B2 | 8/2003 | Kuras |
| 6,610,092 B2 | 8/2003 | Ralph et al. |
| 6,613,090 B2 | 9/2003 | Eckhof et al. |
| 6,626,943 B2 | 9/2003 | Eberlein et al. |
| 6,645,248 B2 | 11/2003 | Casutt |
| 6,645,249 B2 | 11/2003 | Ralph et al. |
| 6,656,224 B2 | 12/2003 | Middleton |
| 6,666,889 B1 | 12/2003 | Commarmond |
| 6,669,730 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,706,068 B2 * | 3/2004 | Ferree ...................... 623/17.11 |
| 6,719,796 B2 | 4/2004 | Cohen et al. |
| 6,723,097 B2 | 4/2004 | Fraser et al. |
| 6,723,127 B2 | 4/2004 | Ralph et al. |
| 6,726,720 B2 | 4/2004 | Ross et al. |
| 6,733,532 B1 | 5/2004 | Gauchet et al. |
| 6,736,850 B2 | 5/2004 | Davis |
| 6,740,117 B2 | 5/2004 | Ralph et al. |
| 6,740,118 B2 | 5/2004 | Eisermann et al. |
| 6,740,119 B2 | 5/2004 | Errico et al. |
| 6,758,861 B2 | 7/2004 | Ralph et al. |
| 6,764,515 B2 | 7/2004 | Ralph et al. |
| 6,770,094 B2 | 8/2004 | Fehling et al. |
| 6,770,095 B2 | 8/2004 | Grinberg et al. |
| 6,793,678 B2 | 9/2004 | Hawkins |
| 6,802,867 B2 | 10/2004 | Manasas et al. |
| 6,827,740 B1 | 12/2004 | Michelson |
| 2001/0016773 A1 | 8/2001 | Serhan et al. |
| 2002/0035400 A1 | 3/2002 | Bryan et al. |
| 2002/0107573 A1 | 8/2002 | Steinberg |
| 2002/0111681 A1 | 8/2002 | Ralph et al. |
| 2003/0009223 A1 | 1/2003 | Fehling et al. |
| 2003/0014112 A1 | 1/2003 | Ralph et al. |
| 2003/0040802 A1 | 2/2003 | Errico et al. |
| 2003/0065395 A1 | 4/2003 | Ralph et al. |
| 2003/0069586 A1 | 4/2003 | Errico et al. |
| 2003/0069643 A1 | 4/2003 | Ralph et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0074074 A1 | 4/2003 | Errico et al. |
| 2003/0078590 A1 | 4/2003 | Errico et al. |
| 2003/0078663 A1 | 4/2003 | Ralph et al. |
| 2003/0078666 A1 | 4/2003 | Ralph et al. |
| 2003/0135277 A1 | 7/2003 | Bryan et al. |
| 2003/0176923 A1 | 9/2003 | Keller et al. |
| 2003/0187454 A1 | 10/2003 | Gill et al. |
| 2003/0187506 A1 | 10/2003 | Ross et al. |
| 2003/0220691 A1 | 11/2003 | Songer et al. |
| 2003/0229355 A1 | 12/2003 | Keller |
| 2003/0229358 A1 | 12/2003 | Errico et al. |
| 2003/0233146 A1 | 12/2003 | Grinberg et al. |
| 2003/0236520 A1 | 12/2003 | Lim et al. |
| 2003/0236571 A1 | 12/2003 | Ralph et al. |
| 2004/0002761 A1 | 1/2004 | Rogers et al. |
| 2004/0002762 A1 | 1/2004 | Hawkins |
| 2004/0010316 A1 | 1/2004 | William et al. |
| 2004/0024462 A1 | 2/2004 | Ferree et al. |
| 2004/0034420 A1 | 2/2004 | Errico et al. |
| 2004/0034421 A1 | 2/2004 | Errico et al. |
| 2004/0034422 A1 | 2/2004 | Errico et al. |
| 2004/0034424 A1 | 2/2004 | Errico et al. |
| 2004/0034425 A1 | 2/2004 | Errico et al. |
| 2004/0034426 A1 | 2/2004 | Errico et al. |
| 2004/0059318 A1 | 3/2004 | Zhang et al. |
| 2004/0073310 A1 | 4/2004 | Moumene et al. |
| 2004/0073312 A1 | 4/2004 | Eisermann et al. |
| 2004/0078079 A1 | 4/2004 | Foley |
| 2004/0083000 A1 | 4/2004 | Keller et al. |
| 2004/0093088 A1 | 5/2004 | Ralph et al. |
| 2004/0098130 A1 | 5/2004 | Ralph et al. |
| 2004/0098131 A1 | 5/2004 | Bryan et al. |
| 2004/0102849 A1 | 5/2004 | Ralph et al. |
| 2004/0111156 A1 | 6/2004 | Ralph et al. |

| | | | | | | | |
|---|---|---|---|---|---|---|---|
| 2004/0117021 | A1 | 6/2004 | Biedermann et al. | EP | 1 421 922 A1 | 5/2004 | |
| 2004/0117022 | A1 | 6/2004 | Marnay et al. | EP | 1 475 059 A2 | 11/2004 | |
| 2004/0133281 | A1 | 7/2004 | Khandkar et al. | FR | 2 694 882 | 2/1994 | |
| 2004/0143331 | A1 | 7/2004 | Errico et al. | FR | 2 730 159 | 8/1996 | |
| 2004/0143332 | A1 | 7/2004 | Krueger et al. | FR | 2 799 116 | 4/2001 | |
| 2004/0148027 | A1 | 7/2004 | Errico et al. | FR | 2 824 261 | 11/2002 | |
| 2004/0158325 | A1 | 8/2004 | Errico et al. | JP | 06178787 A | 6/1994 | |
| 2004/0158328 | A1 | 8/2004 | Eisermann | WO | WO 95/26697 A1 | 10/1995 | |
| 2004/0167534 | A1 | 8/2004 | Errico et al. | WO | WO 99/11203 | 3/1999 | |
| 2004/0167536 | A1 | 8/2004 | Errico et al. | WO | WO 00/23015 | 4/2000 | |
| 2004/0167537 | A1 | 8/2004 | Errico et al. | WO | WO 00/53127 | 9/2000 | |
| 2004/0167626 | A1 | 8/2004 | Geremakis et al. | WO | WO 00/64385 A1 | 11/2000 | |
| 2004/0193158 | A1 | 9/2004 | Lim et al. | WO | WO 01/01893 | 1/2001 | |
| 2004/0220582 | A1 | 11/2004 | Keller | WO | WO 01/01895 A1 | 1/2001 | |
| 2004/0220668 | A1 | 11/2004 | Eisermann et al. | WO | WO 01/18931 A1 | 3/2001 | |
| 2004/0220670 | A1 | 11/2004 | Eisermann et al. | WO | WO 01/19295 | 3/2001 | |
| 2004/0220677 | A1 | 11/2004 | Delfosse et al. | WO | WO 01/64140 | 9/2001 | |
| 2004/0225362 | A1 | 11/2004 | Richelsoph | WO | WO 01/93785 A2 | 12/2001 | |
| 2004/0225363 | A1 | 11/2004 | Richelsoph | WO | WO 01/93786 A2 | 12/2001 | |
| 2004/0225364 | A1 | 11/2004 | Richelsoph et al. | WO | WO 02/080818 A1 | 10/2002 | |
| 2004/0225365 | A1 | 11/2004 | Eisermann et al. | WO | WO 02/089701 A2 | 11/2002 | |
| 2004/0225366 | A1 | 11/2004 | Eisermann et al. | WO | WO 03/003952 A1 | 1/2003 | |
| 2004/0243238 | A1 | 12/2004 | Arnin et al. | WO | WO 03/007779 | 1/2003 | |
| 2004/0243240 | A1 | 12/2004 | Beaurain et al. | WO | WO 03/007780 A2 | 1/2003 | |
| 2004/0249462 | A1 | 12/2004 | Huang | WO | WO 03/007780 A3 | 1/2003 | |
| 2005/0043803 | A1 | 2/2005 | Schultz et al. | WO | WO 03/028595 A1 | 4/2003 | |
| 2006/0036326 | A1* | 2/2006 | Baumgartner et al. ... 623/17.15 | WO | WO 03/039400 A2 | 5/2003 | |
| | | | | WO | WO 03/047472 A1 | 6/2003 | |
| | FOREIGN PATENT DOCUMENTS | | | WO | WO 03/075803 A1 | 9/2003 | |
| DE | 697 22 244 T2 | 5/1998 | | WO | WO 03/075804 | 9/2003 | |
| DE | 197 10 392 C1 | 7/1999 | | WO | WO 03/084449 A1 | 10/2003 | |
| DE | 198 16 832 C1 | 1/2000 | | WO | WO 03/094806 | 11/2003 | |
| DE | 101 52 567 A1 | 5/2003 | | WO | WO 03/099172 A1 | 12/2003 | |
| DE | 203 10 432 U1 | 10/2003 | | WO | WO 2004/016205 A2 | 2/2004 | |
| DE | 203 10 433 U1 | 10/2003 | | WO | WO 2004/019828 A1 | 3/2004 | |
| DE | 203 11 400 U1 | 11/2003 | | WO | WO 2004/026186 A1 | 4/2004 | |
| DE | 203 13 183 U1 | 11/2003 | | WO | WO 2004/039285 A2 | 5/2004 | |
| DE | 203 15 611 U1 | 1/2004 | | WO | WO 2004/041129 A1 | 5/2004 | |
| DE | 203 15 613 U1 | 1/2004 | | WO | WO 2004/041131 A2 | 5/2004 | |
| DE | 20 2004 009 542 U1 | 9/2004 | | WO | WO 2004/054475 A1 | 7/2004 | |
| DE | 20 2004 014 119 U1 | 12/2004 | | WO | WO 2004/054476 A1 | 7/2004 | |
| EP | 0 471 821 B1 | 2/1992 | | WO | WO 2004/054478 A1 | 7/2004 | |
| EP | 471 821 B1 | 2/1992 | | WO | WO 2004/054480 A1 | 7/2004 | |
| EP | 0 282 161 B1 | 8/1992 | | WO | WO 2004/073561 A1 | 9/2004 | |
| EP | 0 560 140 | 9/1993 | | WO | WO 2004/084774 A1 | 10/2004 | |
| EP | 0 560 140 B1 | 9/1993 | | | | | |
| EP | 0 560 141 B1 | 9/1993 | | | OTHER PUBLICATIONS | | |
| EP | 0 634 157 B1 | 1/1995 | | | | | |
| EP | 0 747 025 B1 | 12/1996 | | | | | |
| EP | 1 002 500 A1 | 5/2000 | | | | | |
| EP | 1 344 507 A1 | 3/2002 | | | | | |
| EP | 1 344 508 A1 | 3/2002 | | | | | |
| EP | 1 250 898 A1 | 10/2002 | | | | | |
| EP | 0 948 299 B1 | 5/2003 | | | | | |
| EP | 1 374 808 A1 | 1/2004 | | | | | |
| EP | 1 124 509 B1 | 3/2004 | | | | | |

OTHER PUBLICATIONS

Article from The Burton Report, "Artificial Discs", pp. 5, located at http://www.burtonreport.com/infspine/surgartificialdiscs.htm.

Traynelis, M.D., Vincent, and Haid, Jr., M.D., Regis W., "Spinal Disc Replacement: The Development of Artificial Discs", pp. 12.

Bao, Ph.D., Qi-Bin, and Yuan, M.D., Hansen A., "Artificial Disc Technology", Neurosurg Focus 9(4), 2000, 2000 American Association of Neurological Surgeons, pp. 12.

* cited by examiner

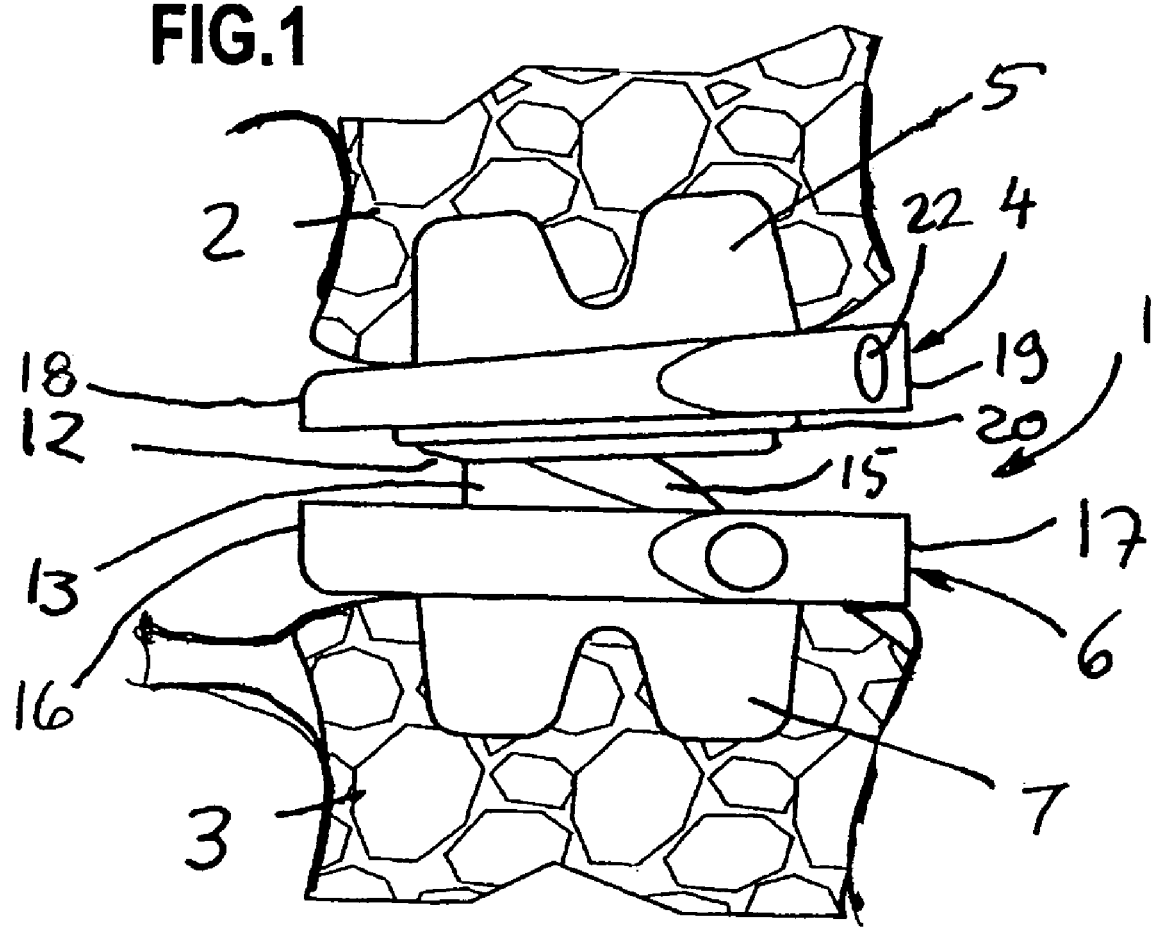

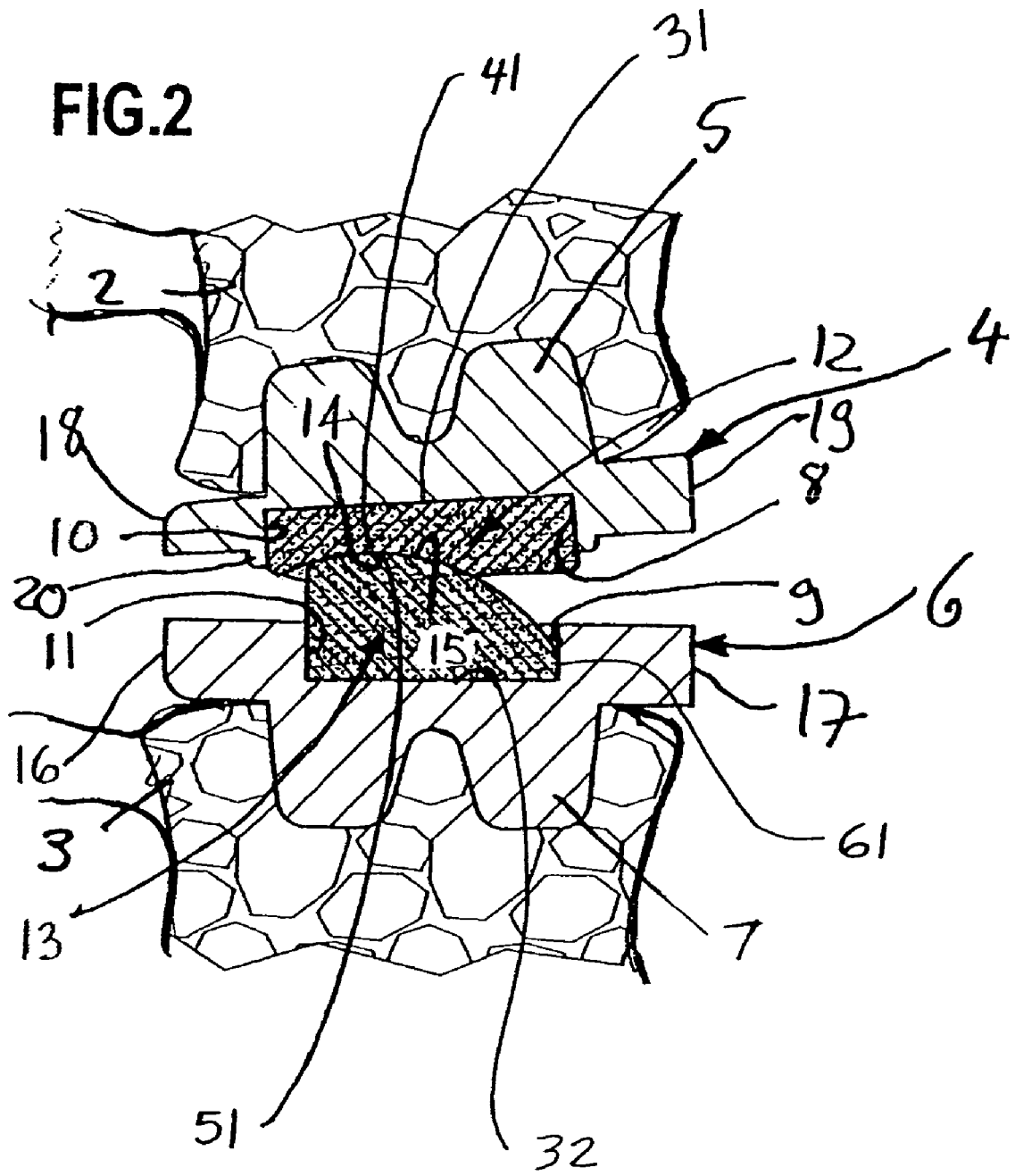

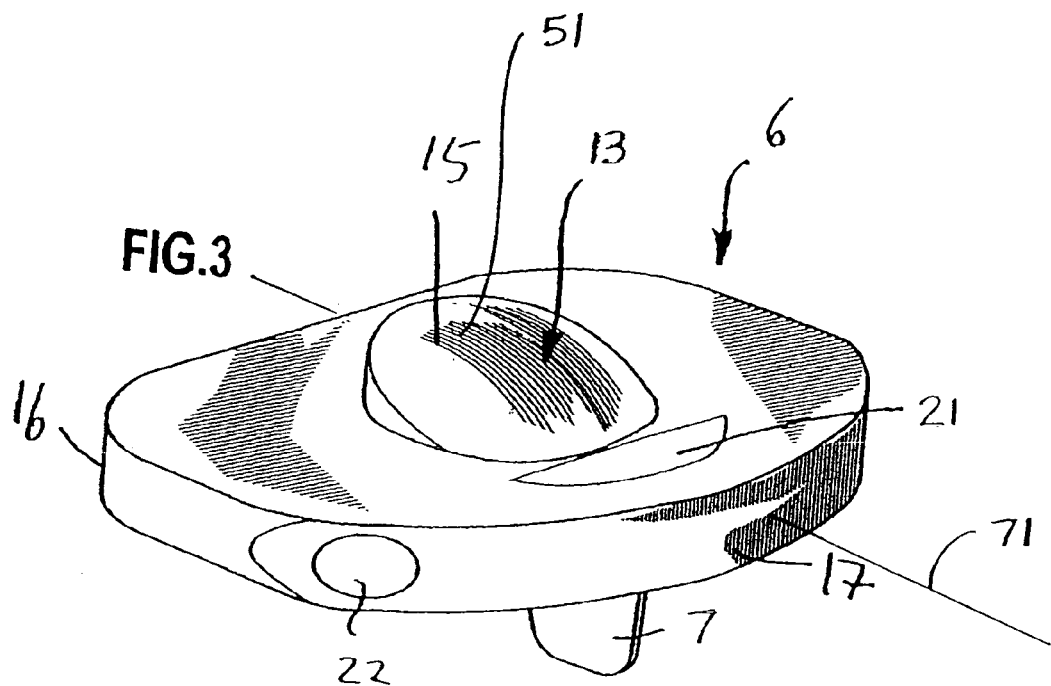
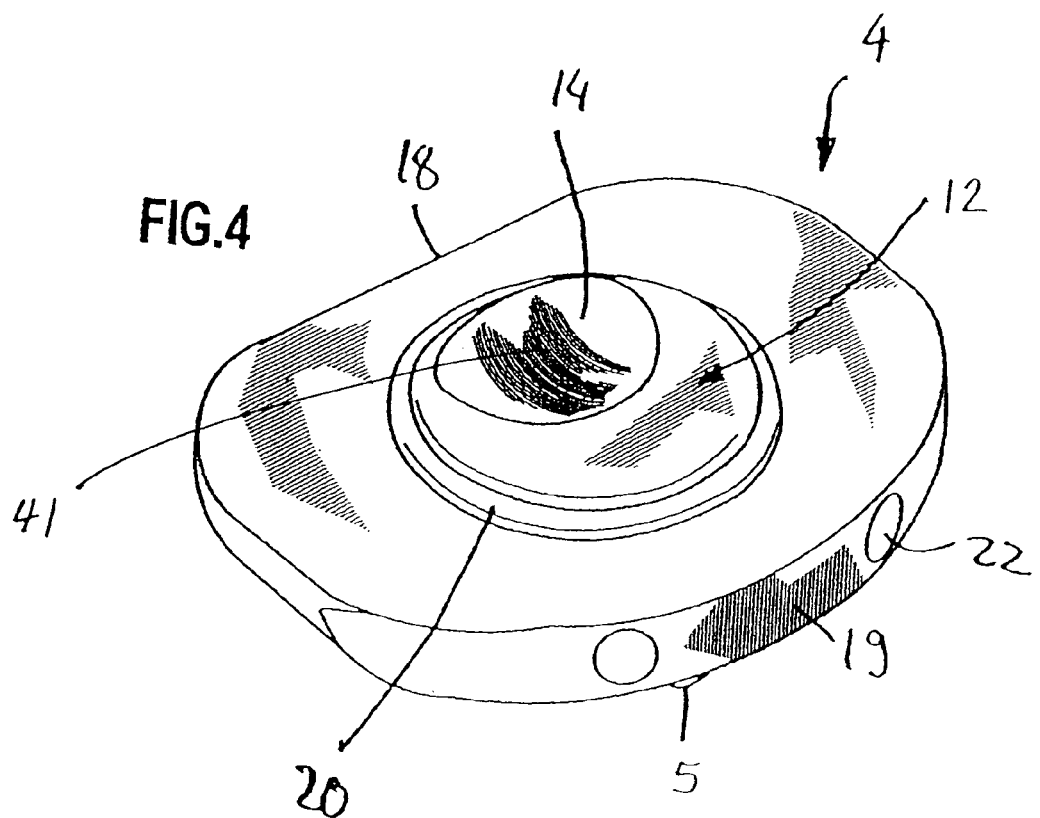

INTERVERTEBRAL IMPLANT

This application is related to and claims the benefit of German Utility Model No. 203 10 432.3 entitled Intervertebral Implant issued on Sep. 18, 2003, and German Patent Application No. 103 30 698.6 filed Jul. 8, 2003.

FIELD OF THE INVENTION

The present invention pertains to an intervertebral implant, with which the original height of the intervertebral disk can be restored in case of, e.g., degeneratively altered intervertebral disks, and the function can be preserved at the same time.

BACKGROUND OF THE INVENTION

Intervertebral implants are known, for example, from U.S. Pat. No. 5,258,031. The displacement of the highest point and of the lowest point of the crowned joint surfaces, i.e., of the plane in which the center of the crowned joint surfaces is located (in the direction of the rear edge of the implant) corresponds to the anatomic conditions. Adjacent vertebral bodies pivot during their mutual pivoting movement around a fulcrum that is located between the middle and the dorsal end of the intervertebral disk, and the ball and socket joint is correspondingly positioned in the dorsal third of the intervertebral disk in the prior-art prosthesis. However, the consequence of this in the prior-art arrangement is that the supporting forces are transmitted to the carrier plates via three relatively small crowned joint surfaces exclusively in the rear third. These carrier plates consequently cannot transmit the supporting forces uniformly to the vertebral bodies, but the supporting forces will occur essentially in the rear third. This may lead to undesired break-ins of the carrier plates in the dorsal area of the vertebral body, especially in the case of weakened vertebral bodies.

Accordingly, there remains a need to improve an intervertebral implant of this class such that uniform introduction of the forces via the vertebral body is also achieved when the fulcrum of the intervertebral implant is displaced in the dorsal direction.

Numerous embodiment variants of such artificial intervertebral disk prosthesis are already known. Many of the prior-art solutions are based on the technical principle of the ball and socket joint.

Thus, WO 01/01893 (Prodisc) describes an intervertebral disk prosthesis with two metallic end plates and an intermediate part made of polyethylene with a convex bearing surface, which slides against a concave surface in one of the two metal plates. The rotation center is located centrally in this prosthesis in the middle between the front and rear edges of the metal plates. U.S. Pat. No. 5,258,031 describes, in contrast, an intervertebral disk prosthesis with a dorsally located rotation center.

The object of the present invention is to optimize the existing designs for intervertebral disk prostheses based on the ball and socket joint principle in terms of wear, kinematics and load distribution.

SUMMARY OF THE INVENTION

The present invention pertains to an intervertebral implant with two carrier plates for being in contact with adjacent vertebral bodies with a convex, crowned joint surface at one carrier plate and with a concave, crowned joint surface at the other carrier plate. The joint surfaces are flatly in contact with one another and pivotably support the carrier plates at each other as a result, and the highest and lowest points of the joint surfaces are positioned between the rear edge and the middle of the carrier plates.

The convex joint surface extends in the middle area of the carrier plate on both sides of the center line of the carrier plate, which center line extends between the front edge and the rear edge to an approximately equal extent and projects at its end facing the rear edge farther away from the carrier plate than at its end facing the front edge. A joint surface is thus obtained that is arranged centrally in the carrier plate and nevertheless forms a fulcrum that is displaced in the dorsal direction, i.e., toward the rear edge. The forces can be introduced approximately centrally over the entire joint surface, so that the risk for one-sided loading of the carrier plates is markedly reduced.

It is especially advantageous if at least one of the joint surfaces is arranged in an inlay that is fixed in the carrier plate; in particular, both joint surfaces may be arranged in such inlays.

It is advantageous if these inlays are inserted into a recess of the carrier plates, so that they are secured against a lateral displacement as a result.

The convex joint surface may pass over into a rear, vertical end surface at its end facing the rear edge.

Provisions may likewise be made for the concave joint surface to pass over into a front, vertical end surface at its end facing the front edge. These end surfaces are now preferably in contact with the side walls of the recess and center the inlay.

The concave joint surface extends now, in particular, up to the end of the inlay facing the rear edge of the carrier plate. Consequently, it is arranged eccentrically in an inlay inserted centrally into the carrier plate, i.e., it is displaced in the direction of the rear edge.

It is favorable if a depression is arranged in the carrier plate with the convex sliding surface between this joint surface and the front edge of the carrier plate. This depression makes it possible to receive parts projecting in case of extreme pivoting angles at the other carrier plate, so that the pivoting angle can be increased as a result.

The sliding surfaces may also be made in one piece with the carrier plates in another embodiment.

It is favorable if the sliding surfaces consist of a ceramic material, and the entire inlay is usually made of ceramic if the sliding surfaces are arranged in an inlay, and carrier plates with corresponding joint surfaces made of ceramic are manufactured if the carrier plates are made in one piece.

BRIEF DESCRIPTION OF THE DRAWINGS

FIG. 1 shows a side view of an intervertebral implant;

FIG. 2 shows a longitudinal sectional view of the intervertebral implant according to FIG. 1;

FIG. 3 shows a perspective top view of one of the two carrier plates of the implant according to FIG. 1; and FIG. 4 shows a perspective top view of the other carrier plate of the implant according to FIG. 1.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The intervertebral implant 1 shown in the figures is used as a replacement for a removed intervertebral disk and is inserted between two vertebral bodies 2, 3. It comprises a first carrier plate 4, which carries rib-shaped projections 5 on its rear side for anchoring in a vertebral body as well as a second carrier plate 6, which likewise carries corresponding projections 7 on its rear side for anchoring in the adjacent vertebral body. The inner sides of the carrier plates 4 and 6, which inner sides face one another, are flat and extend essentially in parallel to one another in the implanted state.

Both carrier plates 4, 6 have on their inner sides a respective central recess 8 and 9 with respective vertical side walls 10 and 11 and with a substantially oval area. A respective joint inlay 12 and 13 made of ceramic is permanently inserted into both recesses 8, 9. A concave, crowned joint surface 14 is milled into one joint inlay 12, and the top side of the other joint inlay 13 is shaped as a convex, crowned joint surface 15. The joint surfaces are designed as partial crowned surfaces and are complementary to one another in a ball and socket joint fashion so that they are flatly in contact with one another and form a pivotable mounting of the two carrier plates 3, 4 as a result. The ceramic components (joint inlays 12 and 13) sliding on one another (joint surfaces 14 and 15) are manufactured with corresponding precision such that the wear in such a ball and socket joint nearly equals zero. A further advantage of the ceramic-on-ceramic bearing is that the problem of creep under load, which is peculiar to polyethylene, is absent.

The convex joint surface 15 extends over the entire top side of the joint inlay 13, and the highest point 51 of the joint surface 15 is displaced in the direction of the rear edge 16 of the carrier plate 6 between the rear edge 16 and a middle area 32 of the carrier plate, i.e., it is not located in the middle of the joint inlay 13 which is arranged centrally between the rear edge 16 and the front edge 17 of the carrier plate 6. Convex joint surface 15 extends in the middle area 32 of the carrier plate 6 on both sides of a center line 71 of the carrier plate, as shown in FIG. 3. As a result, the joint inlay 13, is thicker at its rear edge-side end than it is at its front edge-side end, and the joint surface 15 immerses into the recess 9 at the front edge-side end of the joint inlay 13. The front edge-side end having a front vertical wall surface 61.

The lowest point 41 of concave joint surface 14 is also displaced in its respective joint inlay 12 inserted centrally in the carrier plate 4 in the direction of the rear edge 18 of this carrier plate 4 between rear edge 18 and a middle area 31 of carrier plate 4, while the joint inlay 12 is arranged centrally between this rear edge 18 and the front edge 19 of the carrier plate 4. Displacement of the pivot point in the direction of the rear edge 18, i.e., into the dorsal part of the intervertebral implant 1, is thus acheived. The supporting forces are nevertheless introduced into the carrier plates 4, 6 over a large area and largely centrally so that these carrier plates 4, 6 are loaded centrally, and this load can be transmitted symmetrically to the adjacent vertebral bodies 2, 3 over the entire support surface.

Although the ball and socket joint (joint inlays 12 and 13 with sliding joint surfaces 14 and 15) is arranged centrally in the first and second carrier plates 4, 6, the rotation center is nevertheless displaced in the dorsal direction. This is achieved by the center of the articulating ball radii being arranged eccentrically outside the ball and socket joint.

The joint inlay 13 with the convex joint surface 15 is inserted into a recess 9, which passes directly over into the inner surface of the carrier plate 6. However, the recess 8 of the other carrier plate 4, which receives the joint inlay 12 with the concave joint surface 14, is surrounded by a ring shoulder 20, which projects from the inner side of the carrier plate 4 approximately up to the height of the joint inlay 12 projecting from the recess 8 and is closely in contact with the joint inlay 12, which is supported, as a result, over a greater height in the carrier plate 4.

A depression 21, as shown in FIG. 3, into which the ring shoulder 20 can immerse during the pivoting of the carrier plates 4, 6 in relation to one another, is located in the carrier plate 6 between the recess 9 and the front edge 17, as a result of which the maximum pivot angle can be slightly increased.

Since the ceramic material of the joint inlays 12, 13 has a substantially higher compressive strength and dimensional stability than polyethylene, the dimensions of the crowned joint surfaces 14, 15 may be reduced. The translational motion superimposed to the rotary movement decreases due to the smaller radii. The bearing components (crowned joint surfaces 14, 15) of the intervertebral disk prosthesis 1 may have a radius of 11 mm, for example, which causes a translational motion of approx. 2.3 mm at a flexion angle of 10°.

Plug-in openings 22, as shown in FIGS. 3 and 4, are provided in both carrier plates 4, 6. A handling and insertion tool can be inserted into the plug-in openings 22 to facilitate the insertion of the intervertebral implant 1 into the intervertebral space between the two vertebral bodies 2, 3.

The material of the carrier plates 4, 6 is preferably a biocompatible metal (e.g., a titanium alloy or a chromium-cobalt alloy). However, other materials may be used, e.g., PEEK™, which is a polymer manufactured by Victrex® PLC of the United Kingdom. PEEK™ is transparent to X-rays, which leads to a great advantage in postoperative X-ray diagnostics with CTs or nuclear spin tomography, because, unlike metals, the plastic does not cause any artifacts (i.e., obstructions) in the X-ray image. Finally, the intervertebral disk prosthesis 1 may also be made entirely of ceramic. Because the prosthesis 1 comprises two components, the expense for stocking is greatly reduced and the logistics behind the implant system is substantially simplified.

The joint inlays 12, 13 of the intervertebral disk prosthesis 1 are mounted in the respective first and second carrier plates 4, 6 substantially without clearance, because abrasion may otherwise occur at the ceramic/plate interface because of the hardness of the ceramic material (of the joint inlays 12, 13). This clearance-free mounting/assembly can be achieved, e.g., by means of a conical clamping. However, other possibilities of the clearance-free mounting/assembly can be exhausted as well, such as: shrinking of the metal carrier plates 4, 6 onto the joint inlays 12, 13 by means of thermal expansion; use of elastic intermediate elements (not shown), which compensate a clearance between the joint inlay 12, 13 and the carrier plate 4, 6 due to their intrinsic elasticity/deformation; and additional locking screws (not shown).

In use, the ceramic joint inlays 12, 13 are inserted into the carrier plates 4, 6 prior to implantation, and the intervertebral disk prosthesis 1 is implanted in the assembled state, thereby significantly simplifying the implantation procedure.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. An intervertebral implant for contact with adjacent vertebral bodies, said implant comprising:
   a first carrier plate comprising
      a front edge,
      a middle area,
      a rear edge, and
      a concave, crowned joint surface comprising a lowest point; and
   a second carrier plate comprising
      a front edge,
      a middle area,
      a rear edge,
      a center line extending between said front edge and said rear edge, and
      a convex, crowned joint surface comprising a highest point,
   wherein said joint surfaces are positioned flatly in contact with one another and are configured to support said carrier plates pivotably with respect to one another, said highest and lowest points of said respective convex and concave joint surfaces are positioned between said rear edges and said middle areas of said carrier plates, said convex joint surface extends substantially symmetrically in said middle area of said second carrier plate with respect to said center line of said second carrier plate, and said convex joint surface projects farther away from said second carrier plate at an end facing said rear edge than at an end facing said front edge.

2. The implant of claim 1 further comprising an inlay fixed in at least one of said carrier plates, wherein at least one of said joint surfaces is arranged in said inlay.

3. The implant of claim 2, wherein said carrier plate further comprises a recess for receiving said inlay.

4. The implant of claim 2, wherein said convex joint surface extends to a rear vertical wall surface of said inlay at the end facing said rear edge of said second carrier plate.

5. The implant of claim 2, wherein said convex joint surface extends to a front vertical wall surface of said inlay at the end facing said front edge of said second carrier plate.

6. The implant of claim 2, wherein said concave joint surface extends up to an end of said inlay facing said rear edge of said first carrier plate.

7. The implant of claim 1, wherein said second carrier plate further comprises a depression, said convex joint surface extending between said depression and said rear edge.

8. The implant of claim 1, wherein said joint surfaces are made in one piece with said carrier plates.

9. The implant of claim 1, wherein said joint surfaces are made from a ceramic material.

* * * * *